(12) United States Patent
Pugachev et al.

(10) Patent No.: US 6,504,899 B2
(45) Date of Patent: Jan. 7, 2003

(54) METHOD FOR SELECTING BEAM ORIENTATIONS IN INTENSITY MODULATED RADIATION THERAPY

(75) Inventors: Andrei Pugachev; Lei Xing, both of Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 09/965,585

(22) Filed: Sep. 25, 2001

(65) Prior Publication Data

US 2002/0051513 A1 May 2, 2002

Related U.S. Application Data

(60) Provisional application No. 60/235,244, filed on Sep. 25, 2000.

(51) Int. Cl.[7] .................................................. A61N 5/10
(52) U.S. Cl. ........................................ 378/65; 378/901
(58) Field of Search .............................. 378/4, 64, 65, 378/901

(56) References Cited

U.S. PATENT DOCUMENTS

| | | | |
|---|---|---|---|
| 5,818,902 A | * 10/1998 | Yu | ............................... 378/151 |
| 6,260,005 B1 | 7/2001 | Yang et al. | .................... 703/11 |

OTHER PUBLICATIONS

Rowbottom, et al. "Improvements in Prostate Radiotherapy from the Customization of Beam Directions", Medical Physics, vol. 25, Jul. 1998, pp. 1171–1179.

Rosen, et al., "Treatment Plan Optimization Using Linear Programming", Medical Physics, vol. 18, Apr. 1991, pp. 141–153.

Morill, et al., "The Influence of Dose Constraint Point Placement on Optimized Radiation Therapy Treatment Planning", Int. J. Radiation Oncology Biol. Physics, vol. 19, pp. 129–141.

T. Bortfield, et al., "X–ray Field Compensation with Multileaf Collimators", International Journal of Radiation Oncology, Biology, Physics, vol. 28, 1994, pp. 723–730.

T. R. Mackie, et al., "Tomotherapy", Seminars on Radiation Oncology, vol. 9, 1999, pp. 108–117.

(List continued on next page.)

Primary Examiner—David V. Bruce
(74) Attorney, Agent, or Firm—Lumen Intellectual Property Services

(57) ABSTRACT

A method for selecting an orientation of a treatment beam for intensity modulated radiation therapy based on analysis performed on a model of a patient geometry prior to the actual treatment includes a planning target volume (PTV) and the structures at risk. The method calls for assigning a tolerance parameter to the structures at risk, subdividing the treatment beam into beamlets, selecting a treatment parameter and selecting a set of orientations for the treatment beam and deriving a score for each of the orientations by weighting each of the beamlets so as to maximize the treatment parameter in the PTV while not exceeding the tolerance parameter in the structures at risk at each orientation. The derived scores are used to construct a scoring function to aid in the selection of one or more treatment beam orientations to be used during the actual intensity modulated radiation therapy.

19 Claims, 13 Drawing Sheets

OTHER PUBLICATIONS

C.C. Ling, et al., "Conformal Radiation Treatment of Prostate Cancer Using Inversely–Planned Intensity Modulated Photon Beams Produced with Dynamic Multileaf Collimation", International Journal of Radiation Oncology, Biology, Physics, vol. 35 (1996), pp. 721–730.

S. Webb, "Optimizing the Planning of Intensity–Modulated Radiotherapy", Physics in Medicine and Biology, vol. 39 1994, pp. 2229–2246.

S.V. Spirou and C.S. Chui, "A Gradient Inverse Planning Algorithm with Dose–Volume Constraints", Medical Physics, vol. 25, 1998, pp. 321–333.

R. Mohan, et al., "The Potential and Limitations of the Inverse Radiotherapy Techniques", Radiotherapy & Oncology, vol. 32, 1994, pp. 232–245.

L. Xing, et al., "Fast Iterative Algorithms for 3D Inverse Treatment Planning", Medical Physics, vol. 25, 1998, pp. 1845–1849.

L. Xing and G.T.Y. Chen, "Iterative Methods for Inverse Treatment Planning", Physics in Medicine and Biology, vol. 41, 1996, pp. 2107–2123.

S. Soderstrom, et al., "Which is the Most Suitable Number of Photon Beam Portals in Coplanar Radiation Therapy", International Journal of Radiation Oncology, Biology, Physics, vol. 33, 1995, pp. 151–159.

G.A. Ezzell, "Genetic and Geometric Optimization of Three–Dimensional Radiation Therapy Treatment Planning", Medical Physics, vol. 23, 1996, pp. 293–305.

P. Gokhale, et al., "Determination of Beam Orientations in Radiotherapy Planning", Medical Physics, vol. 21, 1994, pp. 393–400.

M.E. Hosseini–Ashrafi, et al., "Pre–optimization of Radiotherapy Treatment Planning: An Artificial Neural Network Classification Aided Technique", Physics in Medicine and Biology, vol. 44, 1999, pp. 1513–1528.

C.G. Rowbottom, et al., "Beam Orientation Customization using an Artificial Neural Network", Physics in Medicine and Biology, vol. 44, 1999, pp. 2251–2262.

B.C.J. Cho, et al., The Development of Target–Eye–View Maps for Selection of Coplanar or Noncoplanar Beams in Conformal Radiotherapy Treatment Planning, Medical Physics, vol. 26, 1999, pp. 2367–2372.

S.K. Das, et al., "Selection of Coplanar or Noncoplanar Beams using Three–dimensional Optimization Based on Maximum Beam Separation and Minimized Non–Target Irradiation", International Journal of Radiation Oncology, Biology, Physics, vol. 38, 1997, pp. 643–655.

D.L. McShan, et al., "Advanced Interactive Planning Techniques for Conformal Therapy: High Level Beam Description and Volumetric Mapping Techniques", International Journal of Radiation Oncology, Biology, Physics, vol. 33, 1995, pp. 1061–1072.

C.G. Rowbottom, et al., "Constrained Customization of Noncoplanar Beam Orientations in Radiotherapy of Brain Tumors", Physics in Medicine and Biology, vol. 44, 1999, pp. 383–399.

S.L. Sailer, et al., "The Tetrad and Hexad: Maximum Beam Separation as a Starting Point for Noncoplanar 3D Treatment Planning: Prostate Cancer as a Test Case", International Journal of Radiation Oncology, Biology, Physics, vol. 30, 1994, pp. 439–446.

G.T.Y. Chen, et al., "The use of Beam's Eye View Volumetrics in the Selection of Noncoplanar Radiation Portals", International Journal of Radiation Oncology, Biology, Physics, vol. 23, 1992, pp. 153–163.

H.–M. Lu, et al., "Optimized Beam Planning for Linear Accelerator–Based Stereotactic Radiosurgery", International Journal of Radiation Oncology, Biology, Physics, vol. 39, 1997, pp. 1183–1189.

M. Goitein, et al., "Multi–dimensional Treatment Planning: II. Beam's Eye–View, Back Projection, and Projection through CT Sections", International Journal of Radiation Oncology, Biology, Physics, vol. 9, 1983, pp. 789–797.

J. Stein, et al., "Number and Orientations of Beams in Intensity–Modulated Radiation Treatments", Medical Physics, vol. 24, 1997, pp. 149–160.

M Asell, et al., "Optimal Electron and Combined Electron and Photon Therapy in the Phase Space of ComplicationFree Cure", Physics in Medicine and Biology, vol. 44, 1999, pp. 235–252.

T. Bortfield and W. Schlegel, "Optimization of Beam Orientations in Radiation Therapy: Some Theoretical Considerations", Physics in Medicine and Biology, vol. 38, 1993, pp. 291–304.

A. Pugachev, et al., "Beam Orientations in IMRT: To Optimize or not to Optimize?", The Use of Computers in Radiation Therapy, XIII ICCR, 2000, pp. 37–39.

S. Soderstrom and A. Brahme, "Selection of Suitable Beam Orientations in Radiation Therapy using Entropy and Fourier Transform Measures", Physics in Medicine and Biology, vol. 37, 1992, pp. 911–924.

A. Pugachev, A. Boyer, L. Xing, "Beam Orientation Optimization in Intensity–Modulated Radiation Treatment Planning", Medical Physics, vol. 27, 2000, pp. 1238–1245.

M. Braunstein, et al., "Optimum Beam Configurations in Tomographic Intensity Modulated Radiation Therapy", Physics in Medicine and Biology, vol. 45, 2000, pp. 305–328.

* cited by examiner

METHOD FOR SELECTING BEAM ORIENTATIONS IN INTENSITY MODULATED RADIATION THERAPY

RELATED APPLICATIONS

This patent application claims priority from provisional patent application Ser. No. 60/235,244 filed on Sep. 25, 2000 which is herein incorporated by reference.

FIELD OF THE INVENTION

The present invention relates generally to intensity modulated radiation therapy (IMRT) and in particular to the selection of beam orientations by evaluating each beamlet of the beam at various gantry angles prior to treatment.

BACKGROUND OF THE INVENTION

The goal of radiation therapy is to deliver a prescribed dose of radiation usually in the form of electromagnetic radiation (photons), electrons, neutrons or protons to a treatment target, such as a tumor, while sparing adjacent organs at risk (OARs). Intensity modulated radiation therapy (IMRT) adds a new degree of freedom to the conventional three-dimensional radiation therapy and allows one to achieve a better dose distribution by modulating the intensity profiles of the incident beams. For general information on IMRT the reader is referred to T. Bortfield, et. al, "X-ray Field Compensation with Multileaf Collimators", International Journal of Radiation Oncology, Biology, Physics, Vol. 28, 1994, pp. 723–730; T. R. Mackie, et al., "Tomotherapy", Seminars on Radiation Oncology, Vol. 9, 1999, pp. 108–117; C. C. Ling, et al., "Conformal Radiation Treatment of Prostate Cancer using Inversely-Planned Intensity Modulated Photon Beams Produced with Dynamic Multileaf Collimation", International Journal of Radiation Oncology, Biology, Physics, Vol. 35 (1996), pp. 721–730.

In IMRT treatment planning the angles at which radiation is delivered to the treatment site in the patient's body, commonly called gantry angles and couch angles in the case of non-coplanar beams, are usually pre-selected based on experience and intuition of the operator. The corresponding beam intensity profiles are then optimized under the guidance of an objective function using so-called inverse treatment planning methods. General information on these methods is provided by S. Webb, "Optimizing the Planning of Intensity-Modulated Radiotherapy", Physics in Medicine and Biology, Vol. 39, 1994, pp. 2229–2246; S. V. Spirou and C. S. Chui, "A Gradient Inverse Planning Algorithm with Dose-Volume Constraints", Medical Physics, Vol. 25, 1998, pp. 321–333; R. Mohan, et al., "The Potential and Limitations of the Inverse Radiotherapy Techniques", Radiotherapy & Oncology, Vol. 32, 1994, pp. 232–248; L. Xing, et al., "Fast Iterative Algorithms for 3D Inverse Treatment Planning", Medical Physics, Vol. 25, 1998, pp. 1845–1849; and L. Xing and G. T. Y. Chen, "Iterative Methods for Inverse Treatment Planning", Physics in Medicine and Biology, Vol. 41, 1996, pp. 2107–2123.

The prior art teaches numerous approaches to beam orientation selection in conventional radiation therapy and in IMRT. For information on the methods investigated for conventional radiation therapy the reader is referred to the following references: S. Soderstrom, et al., "Which is the Most Suitable Number of Photon Beam Portals in Coplanar Radiation Therapy", International Journal of Radiation Oncology, Biology, Physics, Vol. 33, 1995, pp. 151–159; G. A. Ezzell, "Genetic and Geometric Optimization of Three-Dimensional Radiation Therapy Treatment Planning", Medical Physics, Vol. 23, 1996, pp. 293–305; P. Gokhale, et al., "Determination of Beam Orientations in Radiotherapy Planning", Medical Physics, Vol. 21, 1994, pp. 393–400; M. E. Hosseini-Ashrafi, et al., "Pre-optimization of Radiotherapy Treatment Planning: An Artificial Neural Network Classification Aided Technique", Physics in Medicine and Biology, Vol. 44, 1999, pp. 1513–1528; C. G. Rowbottom, et al., "Beam Orientation Customization using an Artificial Neural Network", Physics in Medicine and Biology, Vol. 44, 1999, pp. 2251–2262; B. C. J. Cho, et al., The Development of Target-Eye-View Maps for Selection of Coplanar or Noncoplanar Beams in Conformal Radiotherapy Treatment Planning", Medical Physics, Vol. 26, 1999, pp. 2367–2372; S. K. Das, et al., "Selection of Coplanar or Noncoplanar Beams using Three-dimensional Optimization Based on Maximum Beam Separation and Minimized Non-Target Irradiation", International Journal of Radiation Oncology, Biology, Physics, Vol. 38, 1997, pp. 643–655; D. L. McShan, et al., "Advanced Interactive Planning Techniques for Conformal Therapy: High Level Beam Description and Volumetric Mapping Techniques", International Journal of Radiation Oncology, Biology, Physics, Vol. 33, 1995, pp. 1061–1072; C. G. Rowbottom, et al., "Constrained Customization of Noncoplanar Beam Orientations in Radiotherapy of Brain Tumors", Physics in Medicine and Biology, Vol. 44, 1999, pp. 383–399; S. L. Sailer, et al., "The Tetrad and Hexad: Maximum Beam Separation as a Starting Point for Noncoplanar 3D Treatment Planning: Prostate Cancer as a Test Case", International Journal of Radiation Oncology, Biology, Physics, Vol. 30, 1994, pp. 439–446; G. T. Y. Chen, et al., "The use of Beam's Eye View Volumetrics in the Selection of Noncoplanar Radiation Portals", International Journal of Radiation Oncology, Biology, Physics, Vol. 23, 1992, pp. 153–163; H. -M. Lu, et al., "Optimized Beam Planning for Linear Accelerator-Based Stereotactic Radiosurgery", International Journal of Radiation Oncology, Biology, Physics, Vol. 39, 1997, pp. 1183–1189; M. Goitein, et al., "Multi-dimensional Treatment Planning: II. Beam's Eye-View, Back Projection, and Projection through CT Sections", International Journal of Radiation Oncology, Biology, Physics, Vol. 9, 1983, pp. 789–797; and Carl Graham, et al., "Improvements in Prostate Radiotherapy from the Customization of Beam Directions", Medical Physics, Vol. 25, 1998, pp. 1171–1179.

Beam orientation selection in IMRT is discussed in the following references: J. Stein, et al., "Number and Orientations of Beams in Intensity-Modulated Radiation Treatments", Medical Physics, Vol. 24, 1997, pp. 149–160; M Åsell, et al., "Optimal Electron and Combined Electron and Photon Therapy in the Phase Space of Complication-Free Cure", Physics in Medicine and Biology, Vol. 44, 1999, pp. 235–252; T. Bortfield and W. Schlegel, "Optimization of Beam Orientations in Radiation Therapy: Some Theoretical Considerations", Physics in Medicine and Biology, Vol. 38, 1993, pp. 291–304; A. Pugachev, et al., "Beam Orientations in IMRT: To Optimize or not to Optimize?", The Use of Computers in Radiation Therapy, XIII ICCR, 2000, pp. 37–39; S. Soderstrom and A. Brahme, "Selection of Suitable Beam Orientations in Radiation Therapy using Entropy and Fourier Transform Measures", Physics in Medicine and Biology, Vol. 37, 1992, pp. 911–924; A. Pugachev, A. Boyer, L. Xing, "Beam Orientation Optimization in Intensity-Modulated Radiation Treatment Planning", Medical Physics, Vol. 27, 2000, pp. 1238–1245; and M. Braunstein, et al., "Optimum Beam Configurations in Tomographic Intensity Modulated Radiation Therapy", Physics in Medicine and Biology, Vol. 45, 2000, pp. 305–328.

Unfortunately, there exists a complex interdependence or coupling between the gantry angles and the beam intensity profiles. In principle, all one needs to do is to add the gantry angle variables into an objective function and then to optimize the objective function with respect to the gantry angles and the beamlet weights. In practice, this brute-force optimization is computationally intensive and hence not very useful because the search space constituted by gantry angles and the beamlet weights cannot be separated into two independent subspaces because of the coupling mentioned above. In addition, the objective function is a non-convex function of the gantry angles and a stochastic sampling of the gantry angles has to be used to avoid trapping in a local minimum. Consequently, computation time required by a complete optimization becomes prohibitively long, making impractical the use of beam orientation optimization for routing clinical applications.

Due to the above-mentioned obstacles, typical IMRT procedures typically involve choosing "optimal" gantry angles first. Then, the beam intensity profiles are optimized. The influence of a set of gantry angles on the final radiation dose distribution in the patient's body is not known until the beam intensity profile optimization is performed. Trial and error attempts are often needed in order to determine a set of good gantry angles for IMRT treatment.

In U.S. Pat. No. 6,260,005 B1 Yang et al. describe an optimization method for arbitrary assessment criteria which can be applied to IMRT beamlet weight optimization and dose calculation. However, just like any other existing systems, no automated or semi-automated computational tool is available for the beam orientation selection. In order to use their system to simulate a radiation treatment generate a treatment plan, it is required that the user to pre-determine the directions of the incident beams and the beam energy before beamlet optimization.

Beam's eye view (BEV) technique was originally used in 3D treatment planning as an interactive tool to assist the oncologists to define radiation portal entry angles that exclude critical structures while fully encompassing the target volume. The binary beam orientation scoring was further improved by the introduction of BEV volumetrics (G. T. Y. Chen, et al., "*The use of Beam's Eye View Volumetrics in the Selection of Noncoplanar Radiation Portals*", International Journal of Radiation Oncology, Biology, Physics, Vol. 23, 1992, pp. 153–163; D. L. McShan, et al., "*Advanced Interactive Planning Techniques for Conformal Therapy: High Level Beam Description and Volumetric Mapping Techniques*", International Journal of Radiation Oncology, Biology, Physics, Vol. 33, 1995, pp. 1061–1072). In this approach, the volume of normal structures intercepted by a specified aperture/portal direction is calculated for all possible incident directions, permitting the planer to evaluate quantitatively the relative merit of a given field direction. In this approach the good beam directions are those minimizing the volume of normal tissue intercepted. While the technique works well for conventional 3D radiation therapy, radical modifications must be made for it to be suitable for IMRT. The problem that we are dealing with now is quite different. The portal shape of each segment and its fractional weight are completely determined by the inverse planning algorithm.

Generally speaking, an intensity modulated beam which intercepts a large volume of sensitive structure(s) is not necessarily a bad beam because of the possibility of partial transmission of part of the incident beam. In reality, it is the dose and/or dose-volume that determines the damage to a sensitive structure (for biology based model, similar technique can be constructed along the line here). Recently Rowbottom et al (C. G. Rowbottom, et al., "*Constrained Customization of Noncoplanar Beam Orientations in Radiotherapy of Brain Tumors*", Physics in Medicine and Biology, Vol. 44, 1999, pp. 383–399) have constructed beam orientation cost function based on beam volumetrics and simple dose model for conventional radiation therapy. In their model, they computed the doses delivered to the target volume and sensitive structures by a uniform-beam with constant weight from each direction. Because there are usually multiple structures intercepting the beam from a given direction, they introduced an empirical trade-off factor to weight each structure to come up with an overall score for each direction. The use of the trade-off factors introduce a great subjectivity into the beam orientation scoring and renders the approach unsuitable for beam orientation selection in IMRT or even in conventional radiation therapy. The underlying shortcoming of the approach is that it did not consider a priori dosimetric knowledge of the system (note that the BEV volumetrics approach is essentially based on a priori geometric information of the system).

Clearly, simple tools and intelligent searches are required in order to provide clinically practical tools for beam orientation selection. Unfortunately, none of the prior art approaches have been able to effectively overcome the challenge of determining optimal gantry angles and beam profiles in a manner that is clinically useful.

OBJECTS AND ADVANTAGES

It is therefore a primary object of the present invention to provide a method for selecting beam orientations for intensity modulated radiation therapy in a manner that does not require excessive computational effort. The method that we wish to construct is a computational method that decouples the fluence profile (the portal and fractional weight of the segments) design and the selection of beam orientation.

Furthermore, it is an object of the invention to provide a method for scoring and selecting gantry angles in a manner which is simple and easy to implement in the clinical environment.

In our technique, the merit of a beam direction should be measured by what that beam could achieve dosimetrically without exceeding the dosimetric or dose-volume constraint of the system. Furthermore, the best achievable scenario of a given beam could be determined based on the a priori dosimetric and geometric information of the given patient.

These and other objects and advantages of the invention will become apparent upon further reading of the specification.

SUMMARY

The objects and advantages are achieved by a method for selecting an orientation of a treatment beam for intensity modulated radiation therapy based on analysis performed on a model of a patient geometry prior to the actual treatment. The model of patient geometry includes a planning target volume (PTV) containing the object to be treated by radiation, e.g., a tumor, and the structure or structures at risk, such as internal organs, bone and/or tissue. The method calls for assigning a tolerance parameter to the structure or structures at risk, subdividing the treatment beam into beamlets, selecting a treatment parameter and selecting a set of angles or orientation for the treatment beam. These orientations typically include gantry angles and couch angles. In the next step, a score is derived for each of the angles in the set by weighting each of the beamlets so as to maximize the treatment parameter in the PTV while not exceeding the tolerance parameter in the structure or structures at risk at each gantry angle. The derived scores are used to construct a scoring function which is essentially the score charted as a function of angle. Based on the scoring function one or more angles are selected as treatment angle(s) to be used during the actual radiation treatment.

In a preferred embodiment, the treatment parameter is a radiation dose. Thus, it is the radiation dose delivered to the PTV which is maximized for each beamlet. The tolerance parameter is also a radiation dose, specifically a tolerance dose for the structure or structures at risk. The various structures at risk, i.e., internal organs, bones and other tissue will each have an associated tolerance dose.

In an alternative embodiment the treatment parameter is an energy rather than radiation dose. In this case the tolerance parameter is still tolerance dose.

In one embodiment the cross section of the beamlets is adjusted in deriving the score. For example, if the beamlets have square beam cross sections, they cay be rotated (collimator rotation). This is done to maximize the treatment parameter, e.g., radiation dose, delivered to the PTV while not exceeding the tolerance parameter in the structure or structures at risk.

It is convenient to divide the model of the patient into voxels and derive the score for each beamlet in each voxel. Preferably, the entire PTV is broken up into voxels and thus the score is obtained for each voxel in the PTV. For example, the score can include computing for the voxels an empiric score $S_i$:

$$S_i = \frac{1}{N_T} \sum_{n \in target} \left(\frac{d_{ni}}{D_T^P}\right)^2,$$

where $d_{ni}$ is the radiation dose delivered to voxel n by beamlet i, $N_T$ is the number of voxels in the PTV, and $D_T^P$ is a prescribed radiation dose.

In one embodiment the method involves calculating a ratio by which the intensity of each beamlet has to be reduced to not exceed the tolerance parameter in the one or more structures at risk. In this case the tolerance parameter is preferably a radiation dose. The limiting value for this radiation dose is typically dictated by many factors, including prior radiation exposure and other considerations known to a person skilled in the art.

As will be apparent to a person skilled in the art, the invention admits of a large number of embodiments and versions. The below detailed description and drawings serve to further elucidate the principles of the invention and some of its embodiments.

DETAILED DESCRIPTION

Figure 1:
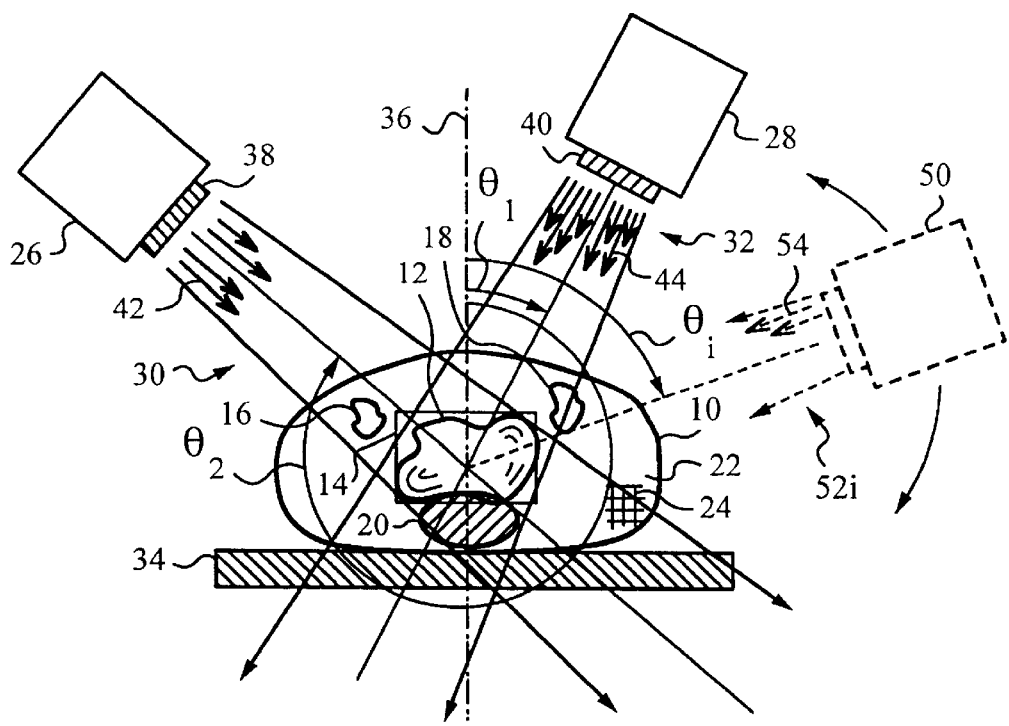
FIG. 1 is a cross sectional plan view of a model of a patient geometry with a planning target volume (PTV) and structures at risk during selection of gantry angles.

The invention will be best understood by first referring to a cross sectional plan view of a model 10 of a patient geometry as shown in FIG. 1. Model 10 is used for planning the beam placement or orientation in an intensity modulated radiation therapy (IMRT) before performing any therapy on the patient. Model 10 is obtained by any suitable technique. For example, computed tomography (CT) and magnetic resonance imaging (MRI) scans of the body can be used to obtain model 10. Both of these techniques are well-known in the art and enable identification of a structure to be treated by IMRT, in this case a tumor 12. For the purposes of IMRT treatment planning tumor 12 is localized within a planning target volume (PTV) 14. In addition, the imaging technique is used to define the location of structure or structures at risk. In this case, structures at risk are internal organs 16, 18, bone 20 and tissue 22.

For ease of computation, entire model 10 is divided into a three-dimensional grid defining a number of voxels 24, of which only a few are indicated in FIG. 1 for reasons of clarity. Voxels 24 are indexed by voxel index n. All voxels 24 within PTV 14 are assigned a treatment parameter value necessary to treat tumor 12. The treatment parameter can be expressed in terms of a radiation dose which is to be delivered to tumor 12 exposure time to radiation and/or various other parameters. Conveniently, the treatment parameter is chosen to be a radiation dose $D_n^P$ prescribed for treating tumor 12. Radiation dose $D_n^P$ is to be delivered to each voxel 24 in PTV 14.

A tolerance parameter is assigned to structures at risk 16, 18, 20, 22, and more specifically, to voxels 24 which structures at risk 16, 18, 20 and 22 occupy. As in the case of the treatment parameter, the tolerance parameter can be expressed in terms of dose and/or other parameters. In the present case the tolerance parameter is chosen to be a tolerance dose $D_n^T$. A person skilled in the art will recognize that tolerance dose $D_n^T$ for each structure at risk 16, 18, 20 and 22 will generally differ and that person will be able to determine the appropriate values.

FIG. 1 shows two sources 26, 28 such as linear accelerators for providing treatment beams 30, 32 at two different orientations with respect to the patient body as determined in accordance with the method of the invention described below. The orientation of treatment beams 30, 32 is typically determined in terms of an angle of a couch 34 on which the patient is positioned, commonly referred to as the couch angle θ, and gantry angles $\theta_1, \theta_2$ at which sources 26, 28 are inclined with respect to the normal 36. Both angles can be varied in discrete increments and in principle continuously over predetermined ranges. For the purpose of the present description, only adjustments in gantry angles $\theta_1, \theta_2$ over the range of 0° to 360° are shown, but it is understood by a person skilled in the art that the couch angle can be adjusted as well. For example, the IEC convention can be used in defining and adjusting both gantry and couch angles. In case of coplanar beam treatment the couch angle can be set to 0°, otherwise the couch angle adjustments can vary in increments of several degrees (e.g., 10°) from −20° to 20° (e.g., for a paraspinal patient treatment) or from −40° to 40° (e.g., for a head-and-neck treatment) for noncoplanar beam treatments. In addition, a person skilled in the art will recognize that the selection of gantry angles $\theta_1, \theta_2$ should be defined with care to avoid possible gantry-patient collision. In practice, the avoidance space depends on the type of linear accelerator and should be determined according to the specifications.

Sources 26, 28 are equipped with beam guiding and shaping mechanisms 38, 40 for subdividing treatment beams 30, 32 into a number of component beams or beamlets 42, 44. Mechanisms 38, 40 generally include leaf collimators (not shown) for collimating beamlets 42, 44 as well as additional lensing devices, apertures, masks and other elements suitable for guiding and shaping of beamlets 42, 44.

Figure 2:
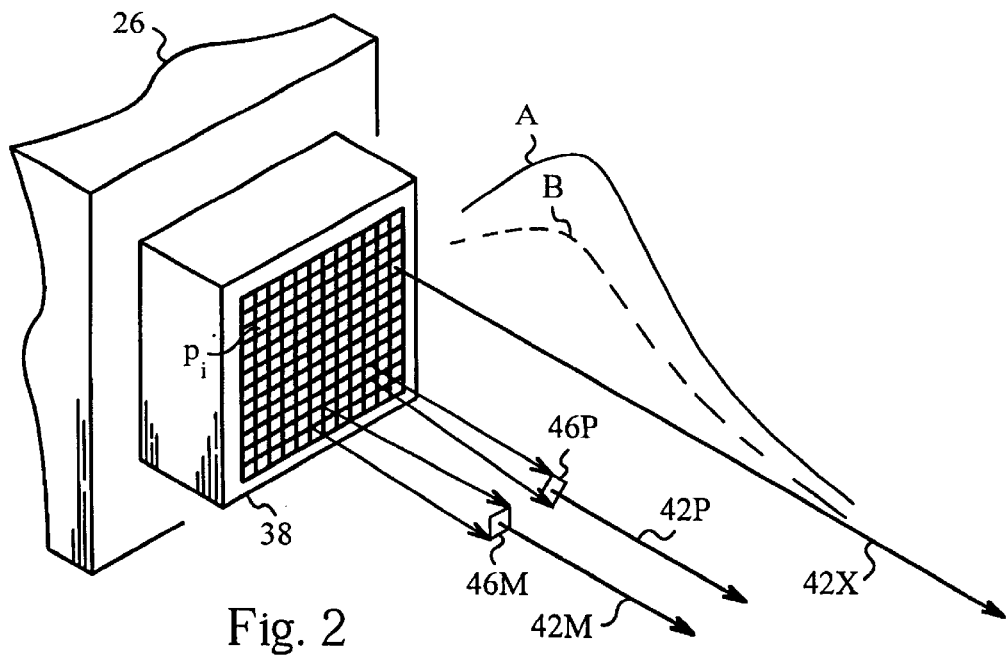
FIG. 2 is an isometric view of a treatment beam source.

FIG. 2 illustrates source 26 generating treatment beam 30 from a number of beamlets 42 with the aid of mechanism 38 in more detail. Specifically, mechanism 38 is drawn to indicate "pixels" $p_i$ corresponding to each beamlet 42. The number of beamlets 42 in beam 30 will depend on the cross section of treatment beam 30 necessary for irradiating PTV 14 at the required resolution as well as on other well-known parameters. Typically, the number of beamlets 42 ranges from a few tens to a few hundred or more.

Source 26 has the capacity of modulating various parameters of beamlets 42. For example, mechanism 38 of source 26 can be used to modulate the cross section of beamlets 42. This is shown on the examples of particular beamlets 42M and 42P. Cross sections 46M, 46P of beamlets 42M and 42P are square or rectangular. Cross section 46P is rotated around the direction of propagation of beamlet 42P by 90°. The rotation can be performed by rotating individual collimators of mechanism 38 corresponding to beamlets 42M, 42P. It should be noted that in current IMRT the cross sections of all beamlets are rotated together.

Source 26 is also capable of modulating the amount of energy in the beamlets. For example, beamlet 42X shows radiation doses A and B as a function of distance from source 26 produced at a high energy and at a low energy. The same collimation and focusing parameters are used at both beamlet energies. The energy levels drop off exponentially with distance and so the doses experience exponential attenuation. Again, in current IMRT the energy in all beamlets is usually altered at the same time. Each beamlet can have an arbitrary intensity through the control of its beamlet-on time by using the multileaf collimator. In other words, source 26 can also modulate the on and off times of beamlets 42.

All of the above beamlet parameters can be adjusted independently or in combination by source 26 and mechanism 38 in attempting to deliver the prescribed radiation dose $DP_n^{64}$ to each voxel 24 in PTV 14. It is understood that source 28 is preferably equivalent to source 26 and enables the same parameter adjustments.

In selecting the orientations of beams 30, 32 for IMRT in accordance with the invention, a set of angles, in this case just gantry angles θ is initially selected for testing. (It is understood that couch angles φ can be included). For example, gantry angles θ from 0° to 360° in equal intervals of 5° can be selected. A computer simulation is then performed observing the effects of positioning a source 50 analogous to actual source 26 or source 28 at each of these gantry angles and emitting a treatment beam 52 made up of beamlets 54. The i-th beam 52i generated by source 50 oriented at the i-th gantry angle $\theta_i$ is indicated in dashed lines. Gantry angles $\theta_1, \theta_2$ actually selected for orienting sources 26 and 28 as shown in FIG. 1 are the final angles or treatment gantry angles determined from the simulation.

In one particular version of the simulation, a parallel beam geometry is used, assuming no scatter and a dose model with exponential attenuation. The attenuation coefficient μ is set to 0.03 cm$^{-1}$, which corresponds to a 5 MV photon treatment beam 52. Gantry angles θ are selected in 5° increments. Each simulated treatment beam 52 is divided into a grid of 1 cm beamlets 54. The two-dimensional (2D) 40 cm×40 cm dose plane is divided into a grid of 5 mm×5 mm pixels. Since target radiation dose $D_n^P$ is generally limited by tolerance dose $D_n^T$ to the adjacent structures at risk 16, 18, 20, 22 the maximum attainable energy for each beamlet 54 is determined based on tolerance doses $D_n^T$ determined for structures at risk 16, 18, 20 and 22. In the present case, maximum allowed doses were selected as tolerance doses $D_n^T$ for organs 16, 18 and bone 20 while tissue 22 was assigned a tolerance dose equal to radiation dose $D_n^P$ prescribed for treatment of tumor 12.

In performing the simulation the i-th simulated treatment beam 52i at i-th gantry angle $\theta_i$ is assumed to be the only treatment beam used for irradiating PTV 14. For each beamlet 54 we find the maximum intensity of electromagnetic radiation that can be used without exceeding the tolerance doses $D_n^T$ for organs 16, 18 and bone 20 located on the path of that beamlet. The quality of each beamlet 54 in beam 52i is thus measured by the maximum achievable intensity in that beamlet. This maximum intensity is essentially the size of the radiation "window" of the corresponding beamlet at gantry angle $\theta_i$. To obtain an overall score of beam 52i, all beamlets 54 are set to their maximum achievable values. In other words, all beamlets 54 are weighted to maximize the radiation dose while not exceeding the tolerance doses for structures at risk 16, 18, 20. In this manner, one obtains the "maximum" intensity profile for gantry angle $\theta_i$ which also represents a score of beam 52i at gantry angle $\theta_i$.

The "maximum" intensity profile is not intended to approximate the optimized beam profile. Instead, it measures the freedom that beam 52i has in terms of the maximum radiation dose deliverable to PTV 14. Conveniently, the dose distribution corresponding to this "maximum" intensity profile is calculated for the voxels in PTV 14 and evaluated using an empiric score $S_i$:

$$S_i = \frac{1}{N_T} \sum_{n \in target} \left(\frac{d_{ni}}{D_T^P}\right)^2$$

where i is the index of gantry angle $\theta_i$, $d_{ni}$ is the radiation dose delivered to voxel n by beam 54 at gantry angle $\theta_i$, $N_T$ is the number of voxels in PTV 14, and $D_T^P$ is the prescribed radiation dose. The higher the deliverable radiation dose, the higher the value of the empiric score. When data on all available beam orientations is available, empiric score $S_i$ can also be expressed in terms of a normalization constant $\bar{d}$ representing the mean radiation dose averaged over all voxels in PTV 14 and all possible orientations (gantry angles $\theta_i$ in the present case). In this case $S_i$ is:

$$S_i = \frac{1}{N_T} \sum_{n \in target} \left(\frac{d_{ni}}{\bar{d}}\right)^2,$$

where $\bar{d}$:

$$\bar{d} = \frac{1}{N_b N_T} \sum_{n \in target} d_{ni},$$

and $N_b$ is the total number of beam orientations available. The use of normalization constant $\bar{d}$ enables the operator to better compare empiric scores $S_i$, since a score function $S_i$ larger than 1.0 implies that the corresponding beam delivers a radiation dose higher than the radiation dose $D_n^P$ prescribed for tumor 12 in PTV 14. Of course, other normalization factors, such as the prescribed radiation dose could also be used. In addition, a person skilled in the art will recognize that the score does not need to be expressed in terms of a square function. In an alternative embodiment any linear ranking function can be used as the score. In yet another embodiment, a ranking function based on a biological modeling scheme can be employed.

The scores $S_i$ for all angles $\theta_i$ are used to construct a scoring function, which is a function of gantry angle $\theta$. The scoring function can be made continuous by interpolating the values between the chosen set of angles $\theta_i$ at which the simulation was actually performed. Conveniently, the scoring function can be plotted versus gantry angle $\theta$ for better visualization and selection of treatment beam orientations. The final selection of treatment beam orientations or gantry angles $\theta_i$ (in FIG. 1 gantry angles $\theta_1$ and $\theta_2$ were selected) is now generally made at gantry angles corresponding to the highest scores. Typically, more than one treatment beam is used and hence several beam orientations are selected. Of course, the operator can use additional considerations known in the art in the final selection.

The calculation and selection procedure is preferably implemented on a computer. For the purpose of creating the appropriate computer routing, the procedure can be restated in the form of the following steps:
1. Find the voxels crossed by the beamlet;
2. Assign the beamlet an intensity that could deliver a dose equal to or higher than the prescription in every target;
3. For each structure at risk or normal tissue voxel crossed by the beamlet, calculate the ratio by which the beamlet intensity has to be reduced to ensure that the tolerance dose is not exceeded;
4. Find the minimum ratio from the data obtained in step 3;
5. Reduce the beamlet intensity assigned in step 2 according to the minimum ratio. This value represents the maximum usable intensity of the beamlet;
6. Repeat steps 1–5 for all relevant beamlets to obtain the "maximum" beam intensity profile in which none of the beamlet intensities can be further increased without violating the tolerance dose of some structure at risk;
7. Perform a forward radiation dose calculation using the "maximum" beam intensity profile;
8. Compute the overall score of the chosen beam orientation according to the empiric score; and
9. Construct the scoring function to be displayed to the operator.

The score function captures the main features of an operator's judgment about the quality of a treatment beam. To gain a better understanding, let us consider a few special cases to illustrate how the score function models the treatment beam orientation selection process. First, consider a case with no dose limiting structures at risk except tissue 22. In this simple case the quality of any gantry angle q depends on the depth of PTV 14 (or surface-to-target distance) and the average number of target voxels 24 covered by a beamlet 54 in treatment beam 52. Both factors are well described by the empiric score. In this special case the tolerance dose of tissue 22 in the entrance zone of treatment beam 52 imposes a limit on the intensity of treatment beam 52. Clearly, when treatment beam 52 has to travel a longer distance to reach tumor 12 will have a lower score because the maximum deliverable radiation dose is low.

Now suppose that we add organ 16 which is at risk between the surface of the body and PTV 14. The score of treatment beam 52 thus depends on both the tolerance dose of organ 16 and the position of organ 16 relative to the skin and PTV 14. The lower the tolerance dose of organ 16 and/or the closer organ 16 is to the skin, the lower the maximum deliverable radiation dose to PTV 14 and the lower the score.

The score and score function do not take into account the dose-volume effect of structures at risk 16, 18, 20 and 22. Inclusion of the dose-volume effect might be important for some parallel structures but does not present any conceptual difficulty. A person skilled in the art will appreciate how to make the necessary adaptations to the scores to include this effect.

EXAMPLES

In order to illustrate the effectiveness of the new method, also termed the pseudo Beam-Eye-View (PBEV) method, we compared the radiation dose distributions obtained with treatment beam orientations selected with PBEV with those obtained with equally spaced treatment beam orientations, as commonly practiced in the prior art. To ensure a fair comparison, a beam intensity profile optimization was performed for both sets of beam orientations. A quadratic objective function of the form:

$$F = \sum_n w_n (D_n - D_n^P)^2,$$

was used for the beam profile optimization. In this objective function $D_n$ is the calculated dose value in voxel n, $D_n^P$ is the desired dose, and $w_n$ is the importance factor assigned to the particular structure. For more information on importance factors the reader is referred to L. Xing, et al., "*Optimization of Importance Factors in Inverse Planning*", *Physics in Medicine and Biology*, Vol. 44, 1999, pp. 2525–2536. Thee summation was performed over all voxels. was equal to the prescribed radiation dose for the target and was equal to zero for structures at risk including normal tissue. An iterative ray-by-ray method was used for beam intensity profile optimization. For more information about beam intensity profile optimization the reader is referred to L. Xing, et al., "*Fast Iterative Algorithms for 3D Inverse Treatment Planning*", Medical Physics, Vol. 25, 1998, pp. 1845–1849.

Selection of treatment beam orientations was performed for three model cases using the PBEV method of the invention. The treatment plans with PBEV selected beam orientations were compared to those with equally spaced beam orientations after using the intensity profile optimization subroutine on each treatment plan. In all cases, the prescribed radiation dose was 1.0 for planning target volume and 0 elsewhere. Tolerance doses were set to 0.3 for structures at risk and 1.0 for normal tissue, unless otherwise specified. The target importance factor was set to 1.0. The importance factors for the structures at risk and normal tissue were defined individually for each case to obtain an acceptable compromise between the target radiation dose coverage and dose avoidance for structures at risk. Five incident treatment beams were used for each treatment plan.

Figure 3:
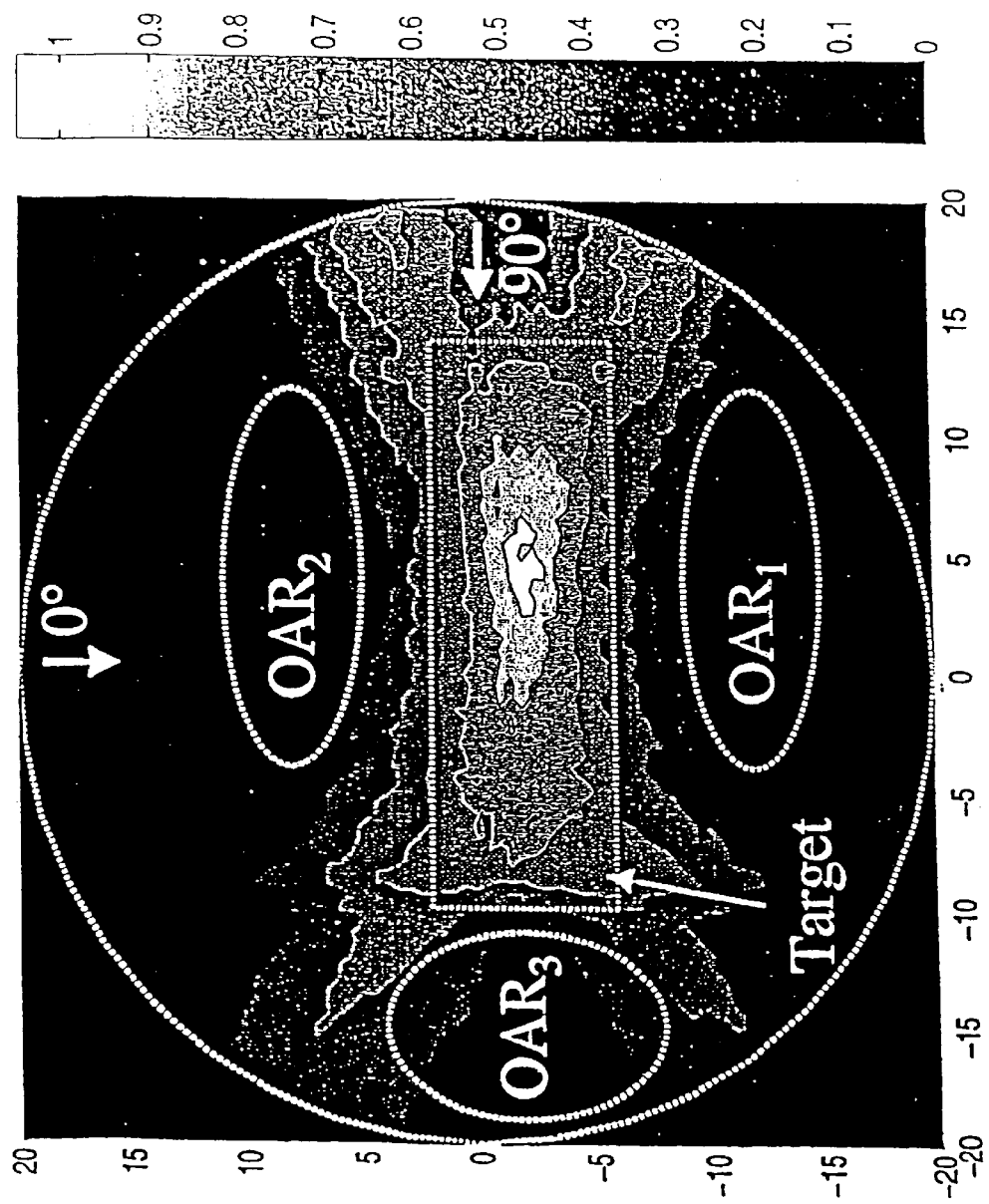
FIG. 3 is a diagram of radiation dose distribution corresponding to treatment beams selected in accordance to the method of invention. The isodose lines represent 20%, 40%, 60%, 80% and 95% of prescribed radiation dose.
Figure 4:
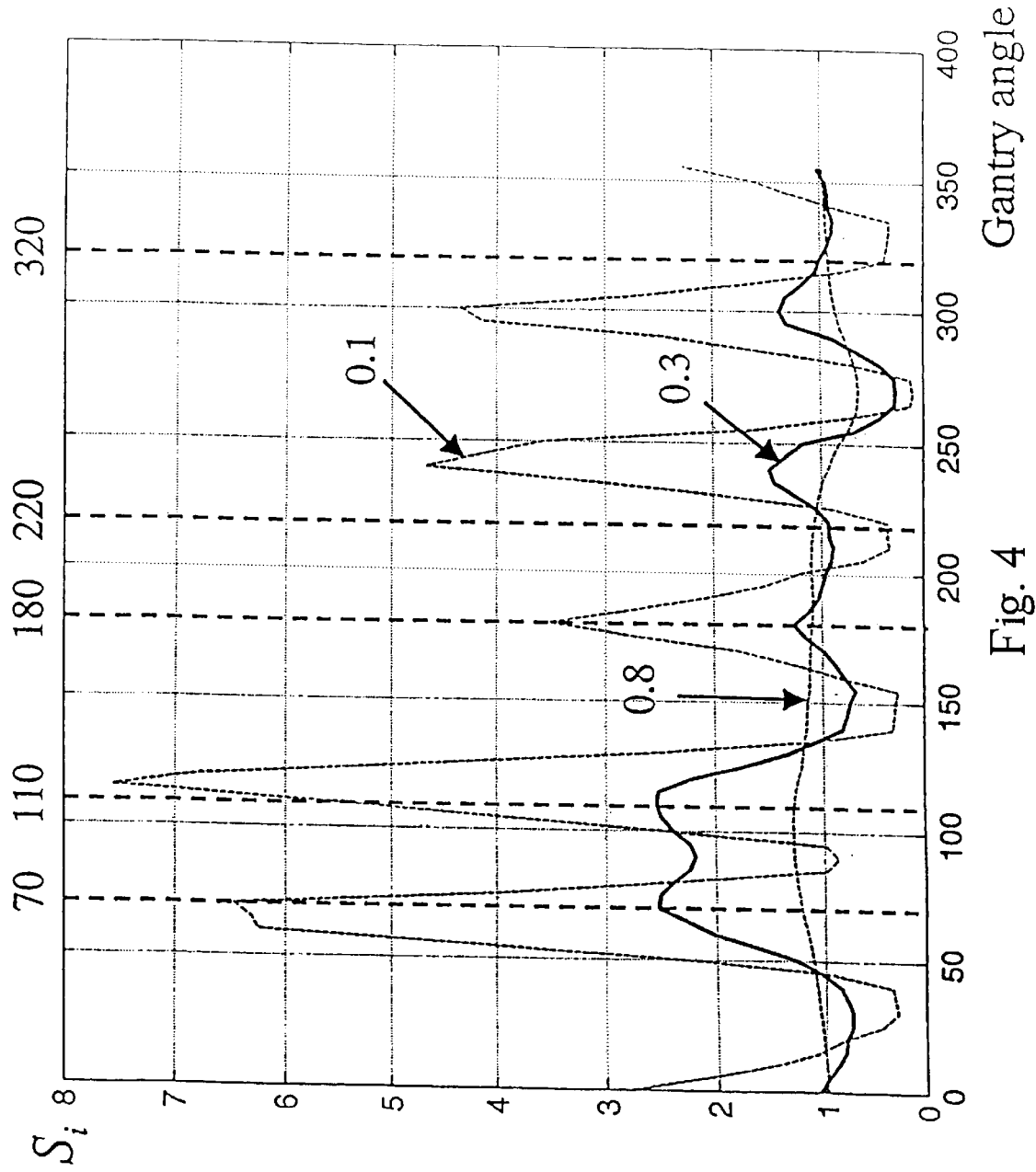
FIG. 4 is a graph of a score function for tolerance parameters equal to 0.1, 0.3 and 0.8 for respective structures at risk. The vertical dashed lines indicate the selection of gantry angles in accordance with the method of invention.

The first case consisted of a rectangular PTV surrounded by three oval organs at risk designated as $OAR_1$, $OAR_2$ and $OAR_3$ in a circular phantom as shown in FIG. 3. In this case, the importance factors $w_n$ were set to 0.2 for the normal tissue and 1.0 for OARs. To illustrate the influence of the tolerance dose for OARs, the PBEV scores were calculated for tolerance doses of 0.1, 0.3 and 0.8. The results are shown in FIG. 4. For OAR tolerance dose of 0.3, the PBEV scoring function shown in FIG. 4 with a thick line peaks at 70° and 110°. This makes intuitive sense since these treatment beams spare $OAR_1$ and $OAR_2$ and deliver lower dose to $OAR_3$. Note that there is a small dip between the scores at 70° and 110° because of increased irradiation of $OAR_3$. This dip becomes larger when the tolerance dose of $OAR_3$ is reduced to 0.1.

The PBEV curve provides useful information to assist in the selection of treatment beam orientations. To place five incident treatment beams optimally, the operator should combine the PBEV technique with empirical experience. The gantry angles selected for this case with $D^T$=0.3 are specified by vertical dashed lines in FIG. 3. This selection was determined by the desire to pick gantry angles with maximum scores while trying to avoid opposed or closely positioned fields. It is well known that configurations with opposed treatment beams are often less effective in IMRT and should be avoided when there are other options. Similarly, a configuration with two closely positioned treatment beams is also suboptimal since the normal tissue dose would be increased in the overlap region. Based on these arguments, we first placed two treatment beams at 70° and 110°. The other two peaks of the PBEV scoring function are located at 240° and 300°. However, treatment beams at these two gantry angles would be opposed to the two previously selected treatment beams. Therefore, we selected 220° and 320° instead. The fifth treatment beam was placed at 180° since there was a peak in the scoring function at this gantry angle. The treatment beam profiles for this set of orientations were optimized using the method described above. The optimized radiation dose distribution is shown in FIG. 3. Isodose lines in the figure correspond to the 20%, 40%, 60%, 80% and 95% of prescribed radiation dose.

Figure 5:
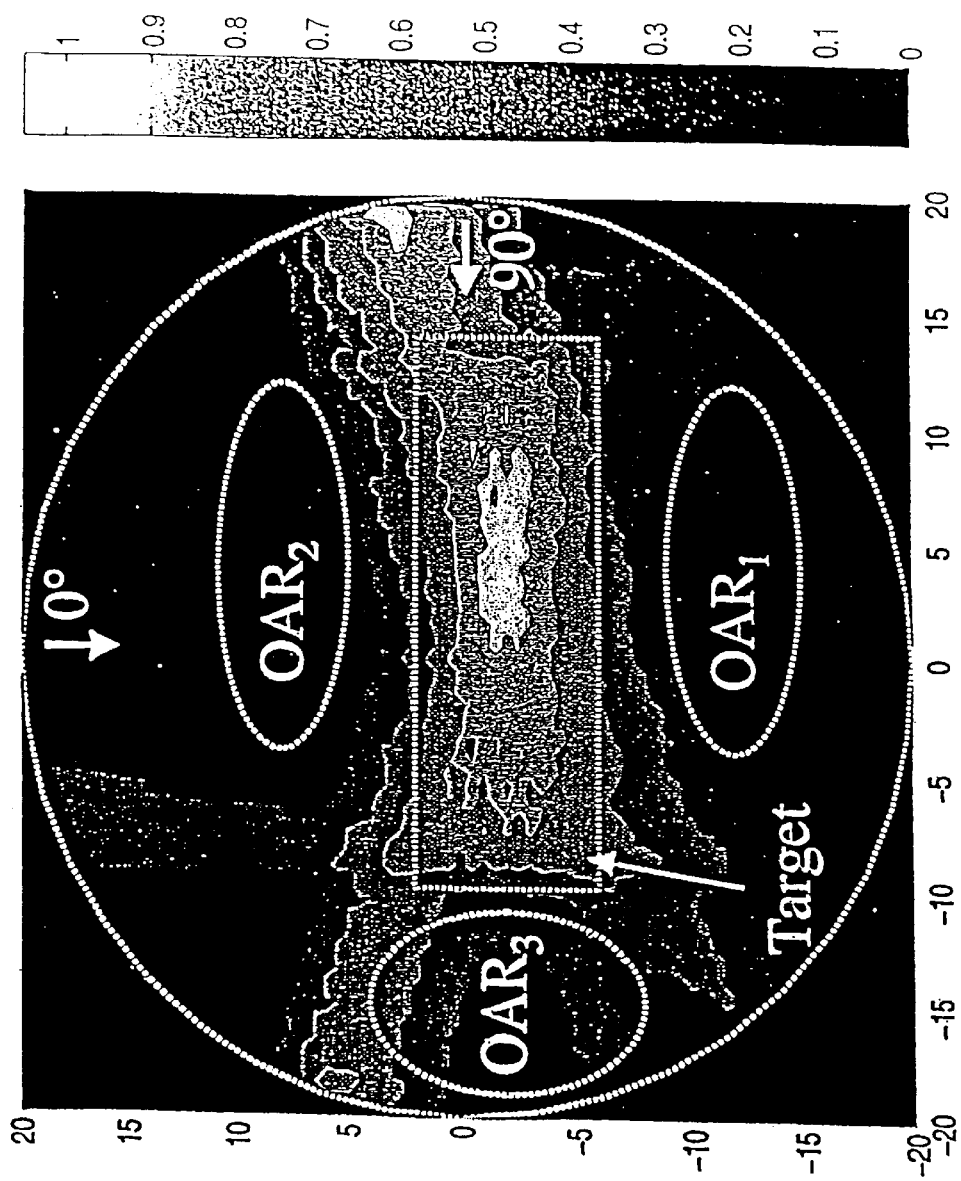
FIG. 5 is a diagram of radiation dose distribution corresponding to five equally spaced treatment beams. Isodose lines represent 20%, 40%, 60%, 80% and 95% of target prescribed radiation dose.

FIG. 3 illustrates the optimized radiation dose distribution obtained with five equiangular spaced treatment beams. The gantry angles for this calculation were 0°, 72°, 144°, 216° and 288°. The target volume and OAR dose volume histograms (DVHs) are shown in FIG. 5. The use of the treatment beam orientations selected with the help of PBEV improved the target radiation dose distribution and resulted in a better OAR sparing. In addition, radiation dose to normal tissue was also significantly reduced, as can be seen from the radiation dose distributions shown in FIG. 3 and FIG. 5.

Figure 6:
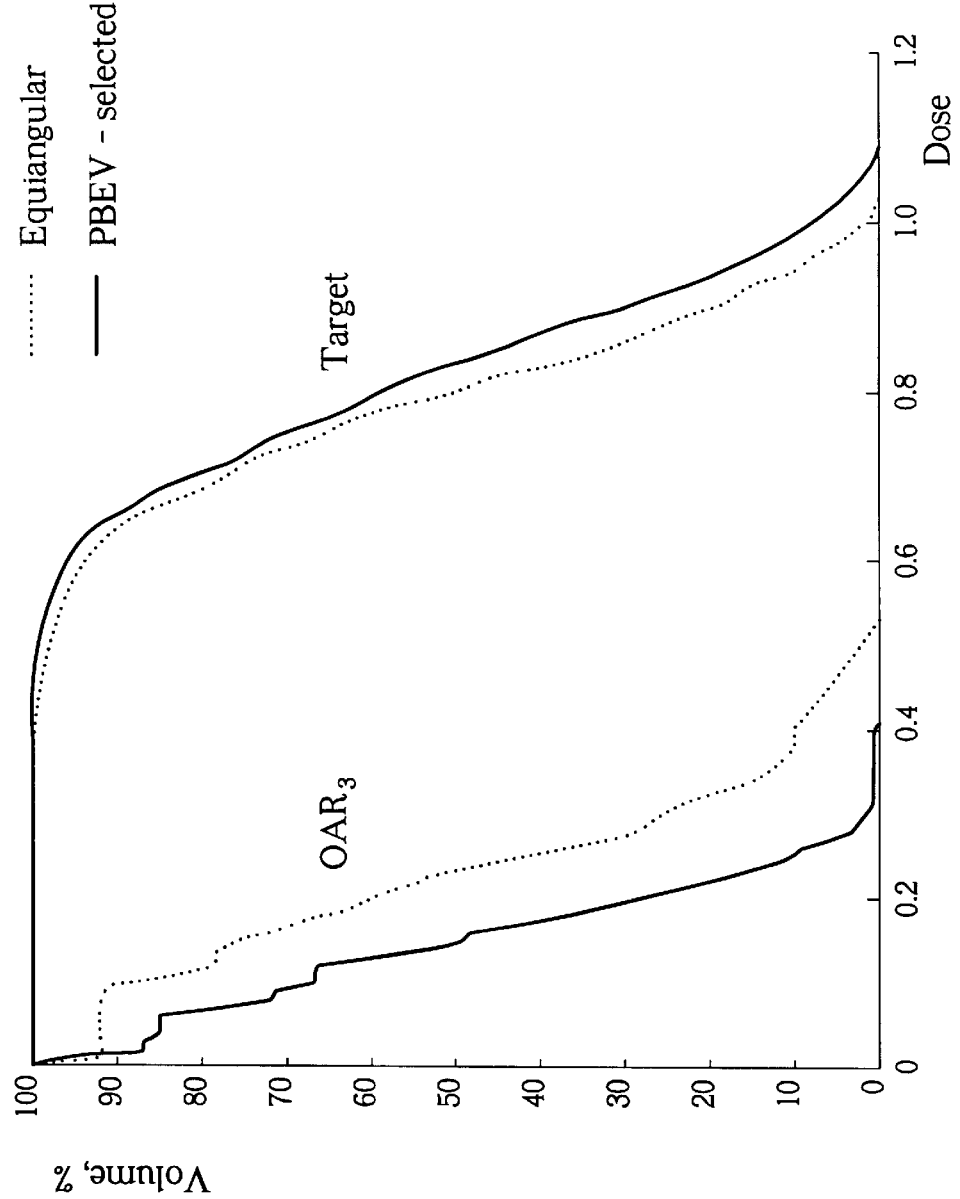
FIG. 6 are dose-volume histograms for the target and $OAR_3$: equiangular spaced treatment beams (dashed line) vs. PBEV selected treatment beams (solid line).
Figure 7:
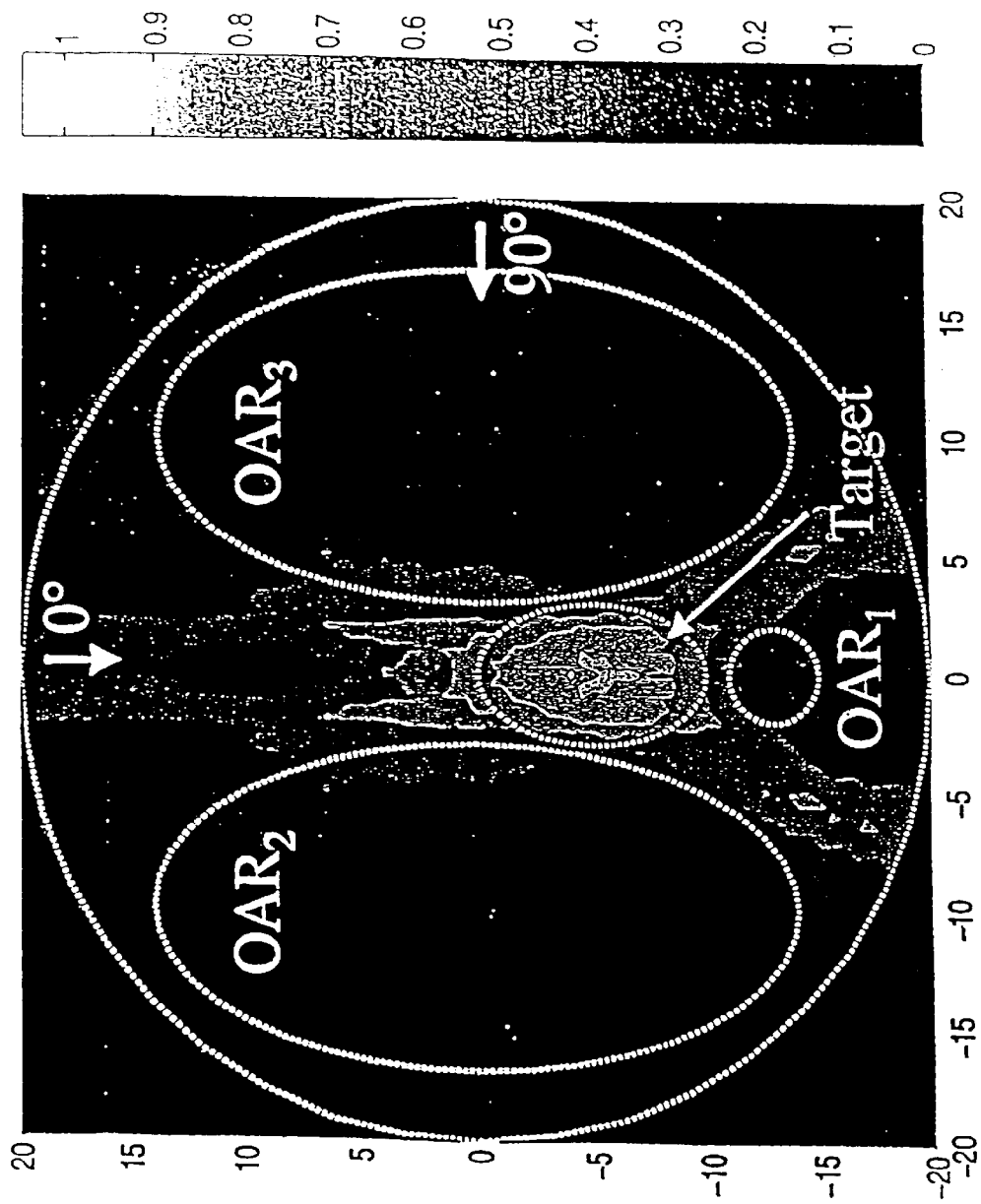
FIG. 7 is a diagram of radiation dose distribution corresponding to the PBEV selected treatment beams. Isodose lines represent 20%, 40%, 60%, 80% and 95% of target prescribed radiation dose.
Figure 8:
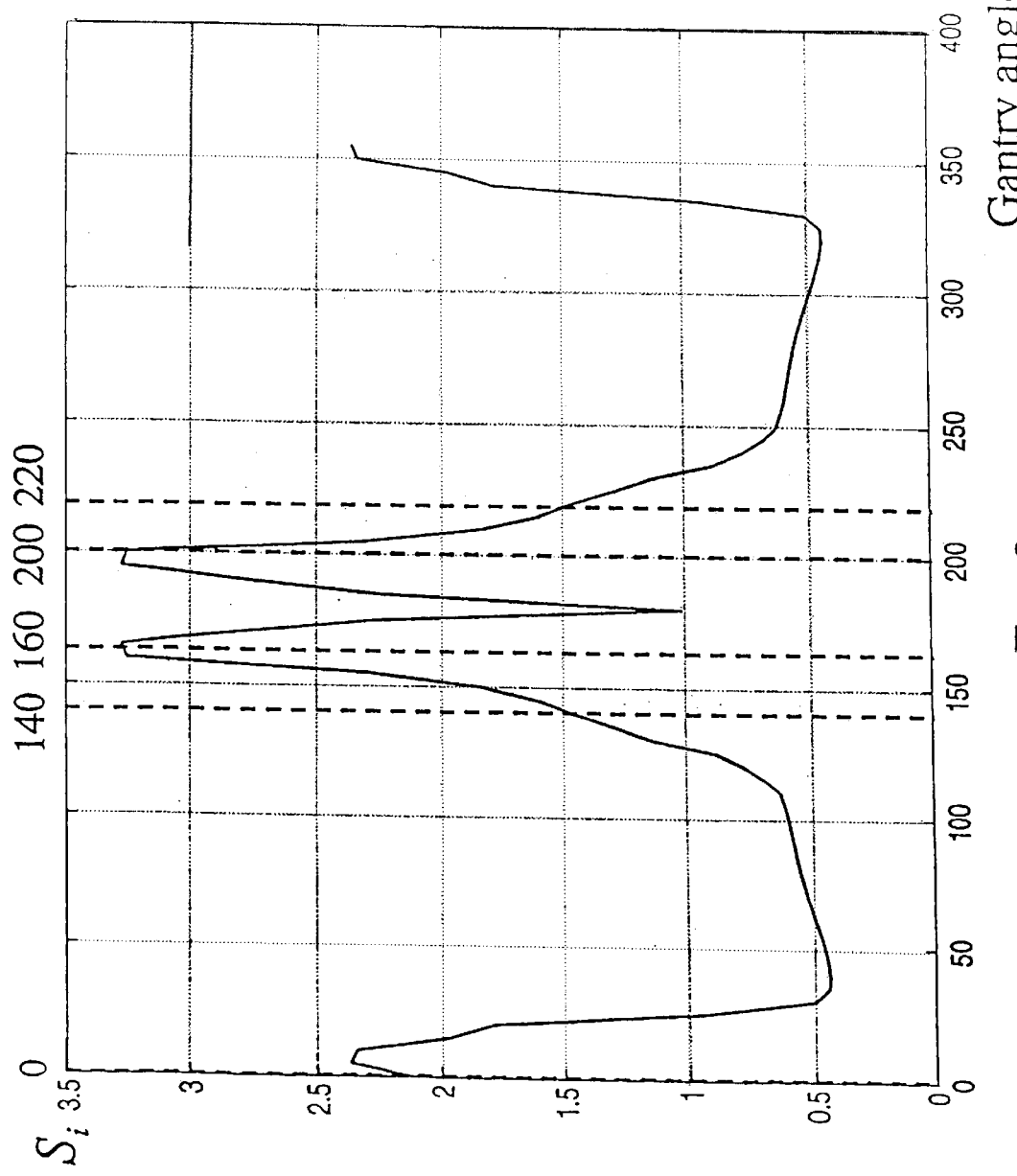
FIG. 8 illustrates PBEV score function and selected gantry angles (vertical dashed lines)
Figure 9:
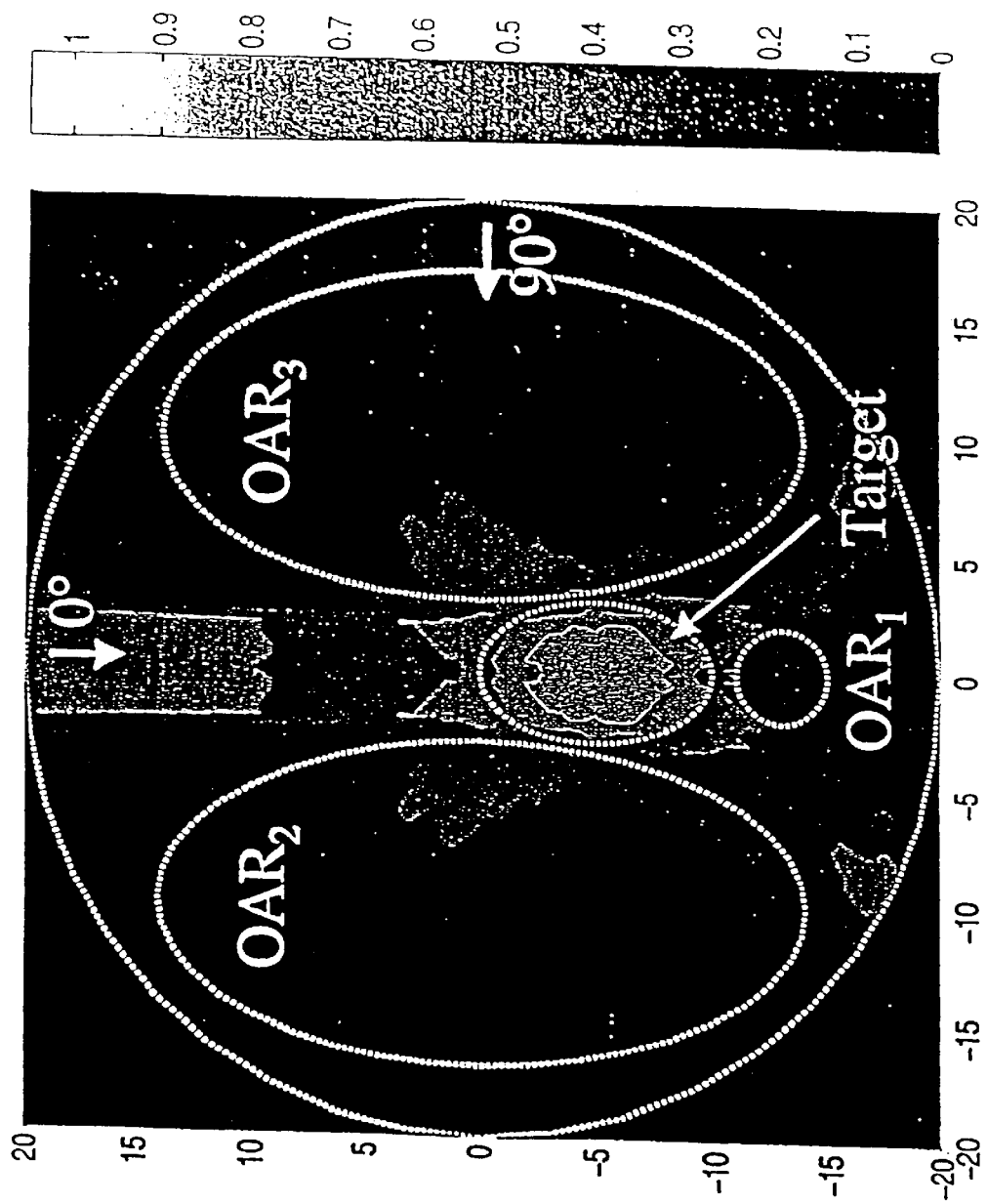
FIG. 9 is a diagram of radiation dose distribution corresponding to five equally spaced treatment beams. Isodose lines represent 20%, 40%, 60%, 80% and 95% of target prescribed radiation dose.
Figure 10:
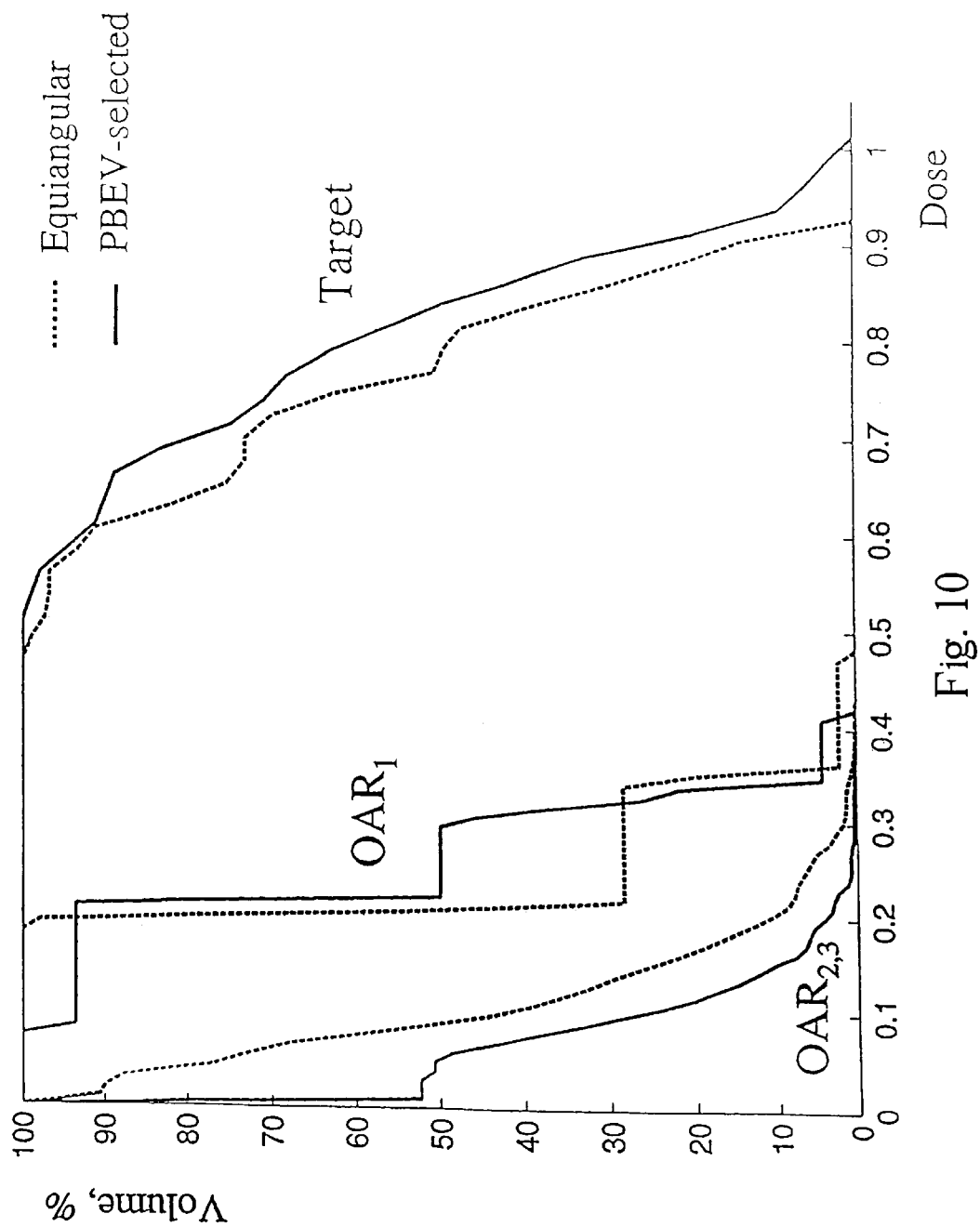
FIG. 10 are dose-volume histograms for $OAR_1$, $OAR_{2,3}$ and target: equiangular spaced treatment beams (dashed line) vs. PBEV selected treatment beams (solid line).

The second case consisted of two oval critical structures and one circular critical structure. The hypothetical target was located in the middle, as shown in FIG. 6. In this case, the assigned importance factor wn was equal to 0.1 for the normal tissue, 0.3 for $OAR_2$ and $OAR_3$, and 0.6 for $OAR_1$. FIG. 8 shows the PBEV score versus gantry angle with vertical dashed lines representing the selected treatment beam gantry angles, which were 0°, 140°, 160°, 200° and 220°. Again, an attempt was made to maximize the value of the scoring function while keeping the treatment beams separated. The optimized radiation dose distribution obtained using this set of beam orientations is shown in FIG. 7. For comparison, we have also carried out the radiation dose optimization for a set of equally spaced treatment beams (at 0°, 72°, 144°, 216° and 288°). The corresponding radiation dose distribution is shown in FIG. 9. A comparison of the target and OAR DVHs is shown in FIG. 10. It can be seen that both the target volume coverage and the OAR avoidance were improved as a result of the PBEV assistance.

Figure 11:
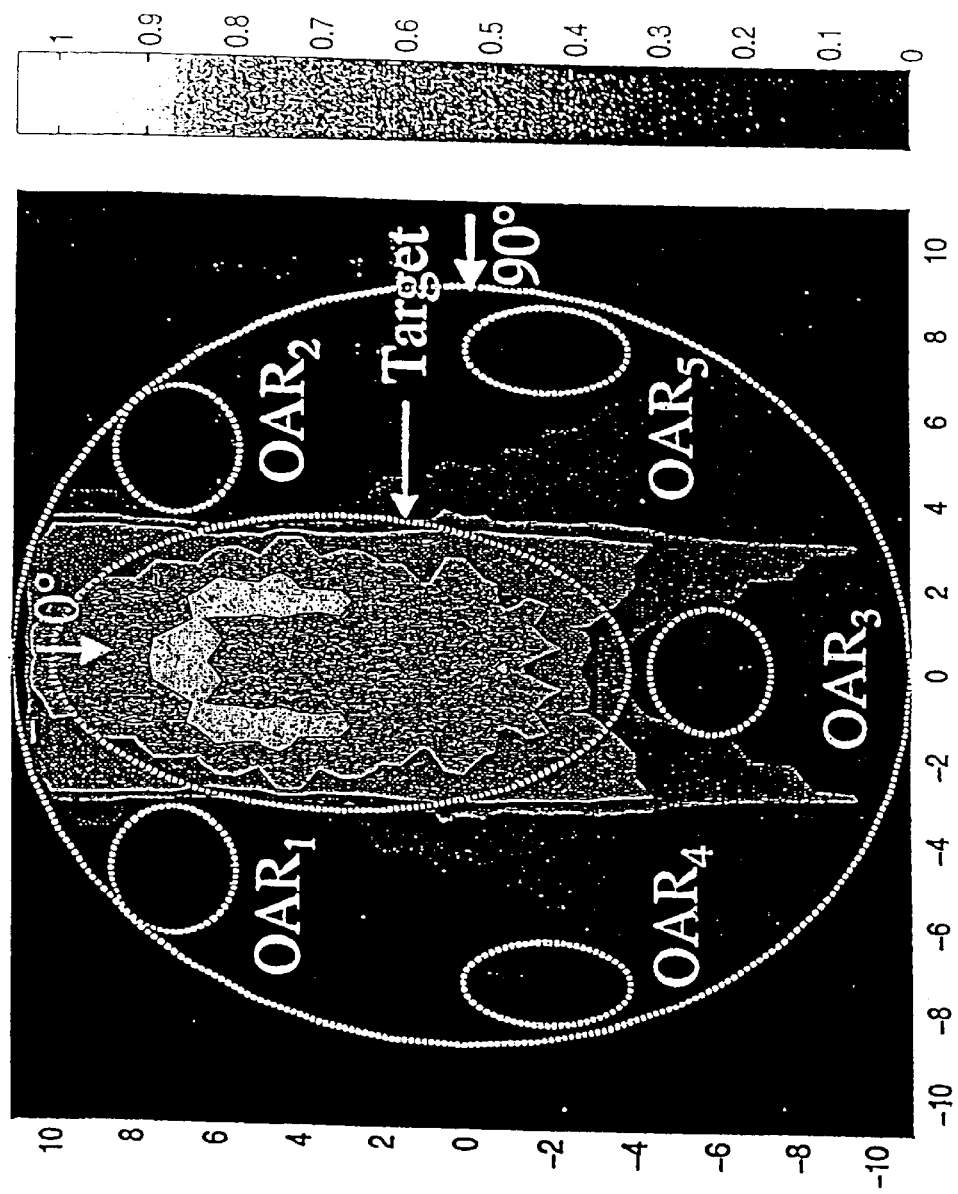
FIG. 11 is a diagram of radiation dose distribution corresponding to the PBEV selected treatment beams. Isodose lines represent 20%, 40%, 60%, 80% and 95% of target prescribed radiation dose.
Figure 12:
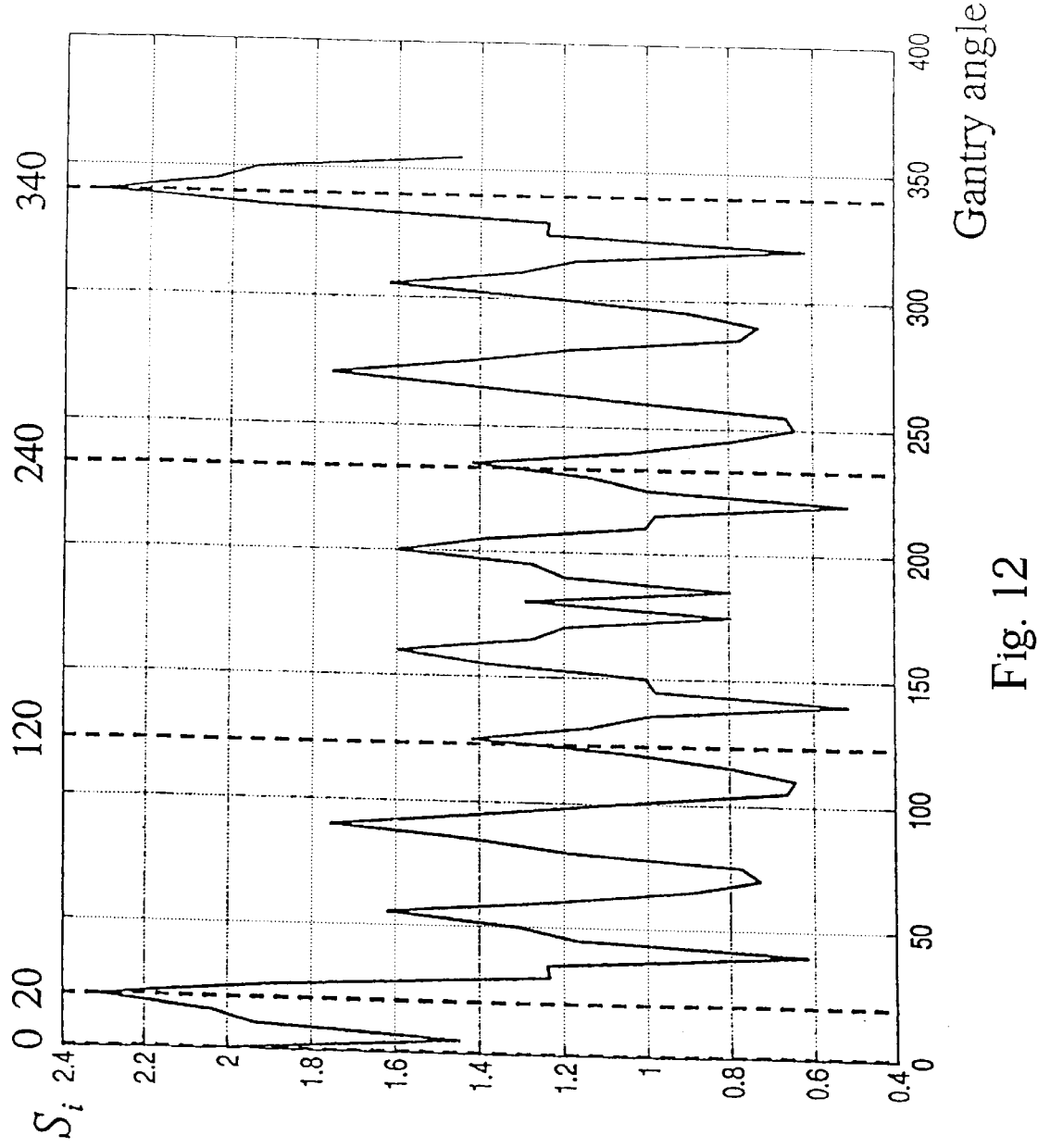
FIG. 12 is a graph of PBEV score function values vs. gantry angles. The positions of the dashed lines indicate the selected gantry angles.
Figure 13:
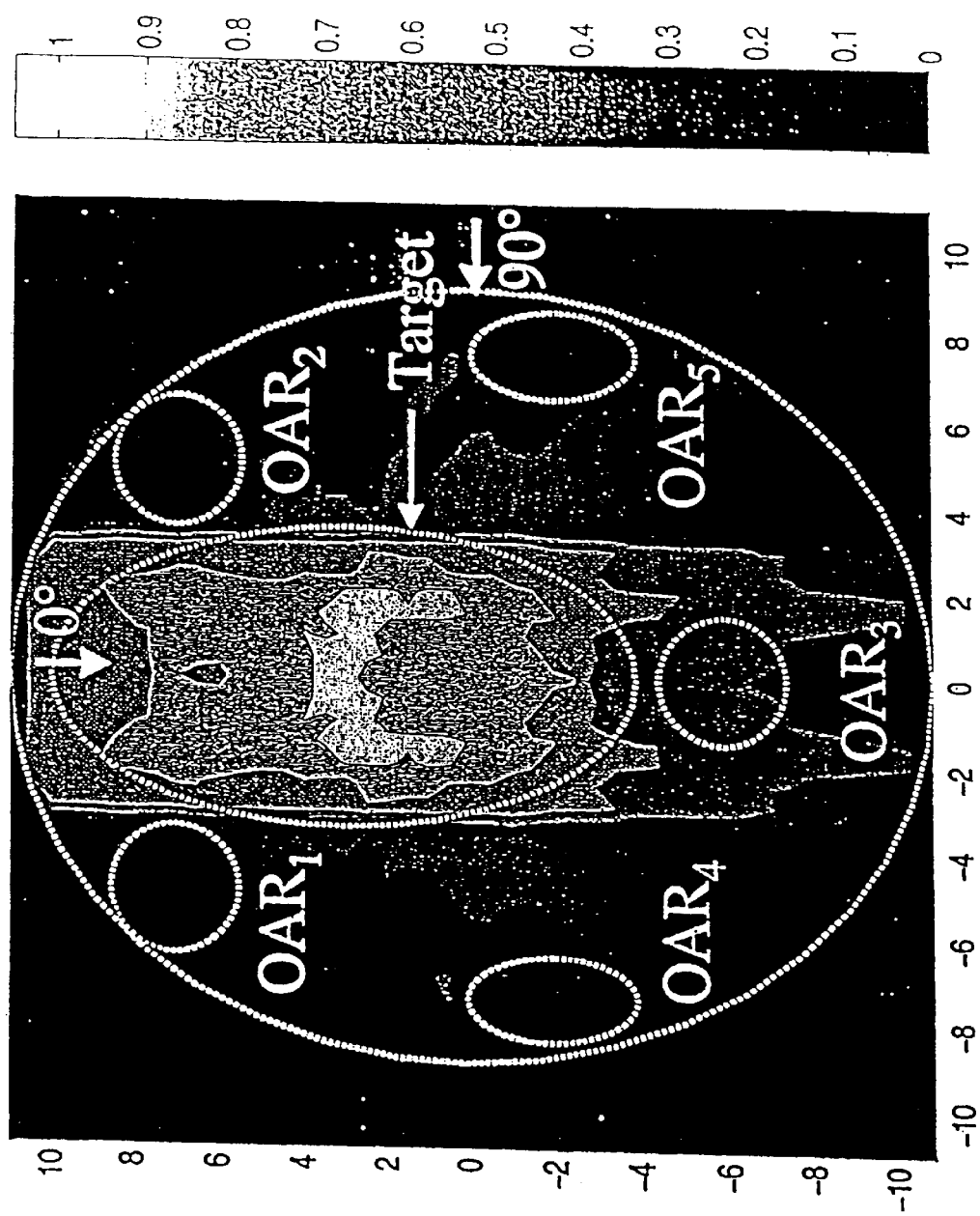
FIG. 13 is a diagram of radiation dose distribution corresponding to five equally spaced treatment beams. Isodose lines represent 20%, 40%, 60%, 80% and 95% of target prescribed radiation dose.
Figure 14:
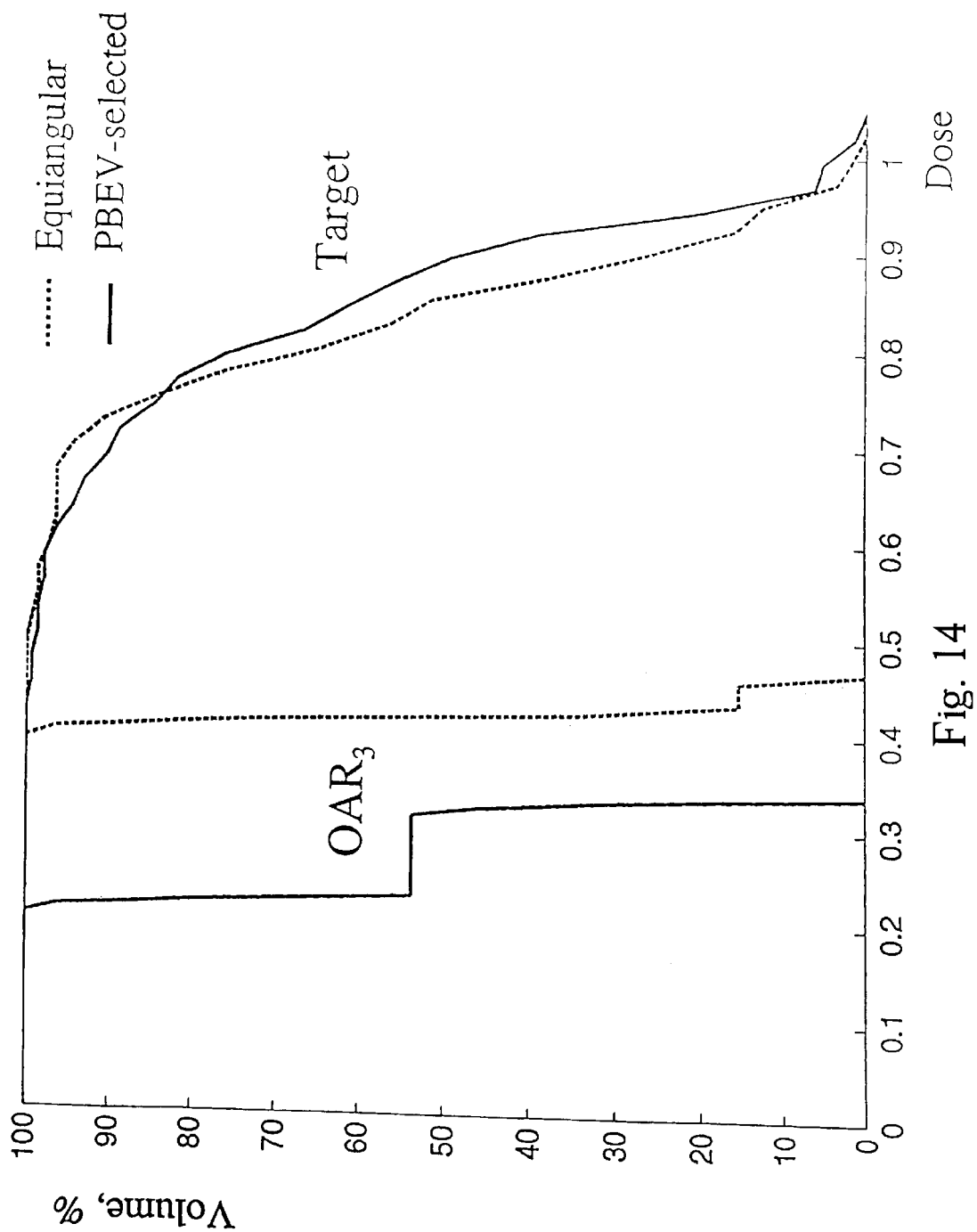
FIG. 14 are dose-volume histograms for the target and $OAR_3$: equiangular spaced treatment beams (dashed line) vs. PBEV selected treatment beams (solid line).

The geometry of the third study is shown in FIG. 11. Five OARs and a target are positioned inside an oval phantom. The importance factors were set to 0.3 for the normal tissue and 2.0 for OARs. The PBEV score versus gantry angle is plotted in FIG. 12. Five vertical dashed lines represent the gantry angles selected for treatment beams. This selection was determined by first putting three treatment beams at 340°, 0° and 20° because there were three main maxima in the PBEV scoring function at those gantry angles. Two remaining treatment beams were positioned at the maxima of the score function at 120° and 240° to spread the treatment beams. The optimized radiation dose distribution obtained for this set of beam orientations is shown in FIG. 11. The radiation dose distribution obtained for a set of equiangular spaced treatment beams (at 0°, 72°, 144°, 216° and 288°) is shown in FIG. 13. A comparison of the DVHs for the target volume and "brainstem" is shown in FIG. 14. Remarkably, the maximum radiation dose to the "brainstem" was reduced by 29%, as can be seen from the DVHs. The DVHs for the other OARs were unchanged.

As can be appreciated from the above description and examples, the method of the invention can be effectively used to assist an operator in the selection of treatment beam orientations in IMRT. An important aspect of the novel technique is that the merit of a beam direction should be measured by what that beam could achieve dosimetrically without exceeding the dosimetric or dose-volume constraint of the system. Furthermore, the best achievable scenario of a given beam could be determined based on the a priori dosimetric and geometric information of the given patient. A person skilled in the art will appreciate that reliance on experience is also important in applying this novel technique, similarly to the use of the BEV tool in conventional radiation therapy. The PBEV method is computationally efficient in comparison with the existing beam orientation optimization algorithms and no excessive computational overhead is required.

The PBEV method can be used in combination with other treatment beam orientation optimization techniques, e.g., simulated annealing. The score function obtained with PBEV can be included as a priori knowledge by serving as a weighting factor of a sampled gantry angle $\theta_i$. The inclusion of the PBEV weighting in the stochastic beam angle sampling process makes it possible to avoid spending valuable computing time on sampling "bad" treatment beam angles and makes the search process more intelligent. This approach should improve the computational efficiency and lead to automated beam orientation selection tool for IMRT planning.

Thus, although the present invention and its advantages have been described in detail, it should be understood that various changes, substitutions, and alterations can be made herein without departing from the principle and the scope of the invention. Accordingly, the scope of the present invention should be determined by the following claims and their legal equivalents.

What is claimed is:

1. A method for selecting an orientation of a treatment beam in intensity modulated radiation therapy, said method comprising:
    a) obtaining a model of a patient geometry comprising a planning target volume and at least one structure at risk;
    b) assigning a tolerance parameter to said at least one structure at risk;
    c) subdividing said treatment beam into beamlets;
    d) selecting a treatment parameter;
    e) selecting a set of angles for said treatment beam;
    f) deriving a score for each angle of said set of angles by weighting each of said beamlets to maximize said treatment parameter in said planning target volume while not exceeding said tolerance parameter in said at least one structure at risk;
    g) constructing a scoring function comprising said score as a function of angle;
    h) selecting at least one treatment angle based on said scoring function.

2. The method of claim 1, wherein said treatment parameter is a radiation dose.

3. The method of claim 2, wherein said tolerance parameter is a tolerance dose.

4. The method of claim 3, wherein said at least one structure at risk is a structure selected from the group consisting of internal organs, bones and tissue.

5. The method of claim 3, wherein said planning target volume comprises a tumor.

6. The method of claim 1, wherein said treatment parameter is an energy.

7. The method of claim 1, further comprising adjusting a beamlet cross section for each of said beamlets to maximize said treatment parameter in said planning target volume while not exceeding said tolerance parameter in said at least one structure at risk.

8. The method of claim 7, wherein said treatment parameter is a radiation dose.

9. The method of claim 1, wherein said at least one structure at risk is a structure selected from the group consisting of internal organs, bones and tissue.

10. The method of claim 1, further comprising dividing said model into voxels.

11. The method of claim 10, wherein said step of deriving said score comprises deriving said score for each of said voxels in said planning target volume.

12. The method of claim 11, wherein said treatment parameter comprises a radiation dose for each of said voxels.

13. The method of claim 12, wherein deriving said score comprises computing for said voxels an empiric score $S_i$:

$$S_i = \frac{1}{N_T} \sum_{n \in target} \left(\frac{d_{ni}}{D_T^P}\right)^2,$$

where $d_{ni}$ is said radiation dose delivered to voxel n by beamlet i with its intensity set to the maximum without exceeding said tolerance dose of said at least one structure at risk, $N_T$ is the number of voxels in said planning target volume, and $D_T^P$ is a prescribed radiation dose.

14. The method of claim 12, wherein said score comprises a function selected from the group consisting of linear ranking functions and biological-modeling based ranking functions.

15. The method of claim 1, further comprising calculating a ratio by which the intensity of each beamlet has to be reduced to not exceed said tolerance parameter in said at least one structure at risk.

16. The method of claim 15, wherein said tolerance parameter is a radiation dose.

17. The method of claim 1, wherein said angle comprises an angle selected from the group consisting of gantry angles and couch angles.

18. The method of claim 1, further comprising selecting at least one of the parameters from the group consisting of collimator angles of said beamlets and energies of said beamlets based on said scoring function.

19. A storage medium tangibly embodying a method for selecting an orientation of a treatment beam in intensity modulated radiation therapy, said method comprising:
    a) obtaining a model of a patient geometry comprising a planning target volume and at least one structure at risk;
    b) assigning a tolerance parameter to said at least one structure at risk;
    c) subdividing said treatment beam into beamlets;
    d) selecting a treatment parameter;
    e) selecting a set of angles for said treatment beam;
    f) deriving a score for each angle of said set of angles by weighting each of said beamlets to maximize said treatment parameter in said planning target volume while not exceeding said tolerance parameter in said at least one structure at risk;
    g) constructing a scoring function comprising said score as a function of angle; and
    h) displaying said scoring function to an operator.

* * * * *